United States Patent
Mixson

(10) Patent No.: US 12,383,632 B2
(45) Date of Patent: Aug. 12, 2025

(54) DOXORUBICIN CONTAINING NANOPLEXES AND USES THEREOF

(71) Applicant: University of Maryland, Baltimore, Baltimore, MD (US)

(72) Inventor: Archibald James Mixson, Rockville, MD (US)

(73) Assignee: University of Maryland, Baltimore, MD (US)

( * ) Notice: Subject to any disclaimer, the term of this patent is extended or adjusted under 35 U.S.C. 154(b) by 778 days.

(21) Appl. No.: 17/442,746

(22) PCT Filed: Mar. 24, 2020

(86) PCT No.: PCT/US2020/024520
§ 371 (c)(1),
(2) Date: Sep. 24, 2021

(87) PCT Pub. No.: WO2020/198263
PCT Pub. Date: Oct. 1, 2020

(65) Prior Publication Data
US 2022/0175958 A1    Jun. 9, 2022

Related U.S. Application Data

(60) Provisional application No. 62/823,121, filed on Mar. 25, 2019.

(51) Int. Cl.
*A61K 47/69* (2017.01)
*A61K 31/65* (2006.01)
*A61K 47/64* (2017.01)
*A61P 35/00* (2006.01)
*B82Y 5/00* (2011.01)

(52) U.S. Cl.
CPC .......... *A61K 47/6927* (2017.08); *A61K 31/65* (2013.01); *A61K 47/6455* (2017.08); *A61P 35/00* (2018.01); *B82Y 5/00* (2013.01)

(58) Field of Classification Search
CPC ............ A61K 47/6927; A61K 47/6455; A61K 31/65; A61P 35/00; B82Y 5/00
See application file for complete search history.

(56) References Cited

U.S. PATENT DOCUMENTS

2017/0296481 A1* 10/2017 Bae .................... A61K 47/6455

FOREIGN PATENT DOCUMENTS

WO   WO-2014153394 A1 *  9/2014  .......... A61K 31/704

OTHER PUBLICATIONS

Chou et al.; Surface-Modified HK:siRNA Nanoplexes with Enhanced Pharmacokinetics and Tumor Growth Inhibition; ACS Publications; Biomacromolecules 2013, 14, 752-760 (Year: 2013).*
Todd et al.; Doxycycline-Regulated p16MTS1 Expression Suppresses the Anchorage-Independence and Tumorigenicity of Breast Cancer Cell Lines that Lack Endogenous p16; Ivyspring International Publisher; Journal of Cancer 2017, vol. 8 190-198 (Year: 2017).*
Chou et al.; Surface-Modified HK:siRNA Nanoplexes with Enhance Pharmacokinetics and Tumor Growth Inhibition; ACS Publications; Biomacromolecules, 2013. 14, 752-760 (Year: 2013).*
Leng et al.; Increased tumor distribution and expression of histidine-rich plasmid polyplexes; Wiley Online Library; J Gene Med 2014; 16: 317-328. (Year: 2014).*

* cited by examiner

*Primary Examiner* — Robert A Wax
*Assistant Examiner* — John W Lippert, III
(74) *Attorney, Agent, or Firm* — Benjamin Aaron Adler

(57) ABSTRACT

The present invention provides tumor-targeting nanoplexes. Generally, a tumor-targeting nanoplex is a chemotherapeutic agent DNA conjugate with a first tumor-targeting agent and an optional second tumor-targeting agent linked thereto, such as a doxorubicin plasmid DNA conjugate and a linear histidine-lysine peptide with an optional cRGD-PEG-H3K4b second targeting agent. Also provided are methods for treating a cancer in a subject and for decreasing growth of a tumor in a cancer in a subject in need thereof in which the tumor targeting nanoplex is administered.

24 Claims, 6 Drawing Sheets

Specification includes a Sequence Listing.

SEQUENCE LISTING

<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Common motif in linear H2K peptides
<220> FEATURE:
<221> NAME/KEY: misc_feature
<222> LOCATION: (2)..(3)
<223> OTHER INFORMATION: Xaa is any amino acid

<400> SEQUENCE: 1

Lys Xaa Xaa Lys
1

<210> SEQ ID NO 2
<211> LENGTH: 4
<212> TYPE: PRT
<213> ORGANISM: Artificial Sequence
<220> FEATURE:
<223> OTHER INFORMATION: Histidine lysine peptide motif

<400> SEQUENCE: 2

Lys His His Lys
1

<210> SEQ ID NO 3
<211> LENGTH: 20
<212> TYPE: PRT
<213> ORGANISM: Artificial Sequence
<220> FEATURE:
<223> OTHER INFORMATION: Amide-capped histidine lysine peptide H2K
<220> FEATURE:
<221> NAME/KEY: misc_feature
<222> LOCATION: (20)
<223> OTHER INFORMATION: C-terminal histidine is amide-capped

<400> SEQUENCE: 3

Lys His Lys His His Lys His His Lys His His Lys His His Lys
1               5                   10                  15

His His Lys His Lys
            20

<210> SEQ ID NO 4
<211> LENGTH: 20
<212> TYPE: PRT

```
<213> ORGANISM: Artificial Sequence
<220> FEATURE:
<223> OTHER INFORMATION: Histidine lysine peptide H2K-CO2H

<400> SEQUENCE: 4

Lys His Lys His His Lys His His Lys His His Lys His His Lys
1               5                   10                  15

His His Lys His Lys
            20

<210> SEQ ID NO 5
<211> LENGTH: 33
<212> TYPE: PRT
<213> ORGANISM: Artificial Sequence
<220> FEATURE:
<223> OTHER INFORMATION: Histidine lysine peptide H2K-CO2H

<400> SEQUENCE: 5

Lys His His Lys His His Lys His His His Lys His His His Lys
1               5                   10                  15

His His His Lys His His His Lys His His Lys His His Lys
            20                  25                  30

His His Lys
```

DOXORUBICIN CONTAINING NANOPLEXES AND USES THEREOF

CROSS-REFERENCE TO RELATED APPLICATION

This is a national stage application under 35 U.S.C § 371 of pending international application PCT/US2020/024520, filed Mar. 24, 2020, which claims benefit of priority under 35 U.S.C. § 119(e) of provisional application U.S. Ser. No. 62/823,121, filed Mar. 25, 2019, the entirety of both of which is hereby incorporated by reference.

BACKGROUND OF THE INVENTION

Field of the Invention

The present invention relates to the fields of drug delivery, pharmacology and cancer chemotherapy. More specifically, the present invention relates to a nanoplex composition for the targeted therapeutic treatment of tumors and methods of treating tumors using nanoplex compositions.

Description of the Related Art

Doxorubicin is a common first-line therapy for numerous cancers including breast, ovarian, bladder, and lung. Although the mechanism of action for doxorubicin is still being studied, several mechanisms have been proposed including intercalation into DNA disrupting gene expression, generation of reactive oxygen species, and inhibition of topoisomerase II (1). Regardless of whether one or several of these proposed mechanisms are in play, doxorubicin has cell-cycle specific activity and binds to DNA with high affinity.

The most severe long-term adverse effect of doxorubicin therapy is irreversible cardiomyopathy, an effect related to the total cumulative dose (2). Increased levels of reactive oxygen species resulting in apoptosis in the heart appear to have a significant role in doxorubicin cardiomyopathy. Efforts to mitigate doxorubicin cardiomyopathy and other adverse effects have been undertaken via liposomal drug delivery (1,3). Several systemically administered liposomal doxorubicin formulations have been investigated and approved including pegylated (DOXIL, a doxirubicin liposomal product of the ALZA Corporation) and unpegylated forms. Importantly, there is a better safety profile with liposomal doxorubicin formulations (1,4).

There has been a debate as to whether pegylated or non-pegylated liposomal doxorubicin increased survival in cancer patients (1,5) with one notable exception. In cancer patients with cardiac disease, liposomal doxorubicin improves survival compared to conventional doxorubicin (5). These liposomal nanoparticles enter the tumors preferentially through the enhanced permeability and retention (EPR) effect. The enhanced permeability and retention effect is thought to result from a combination of leakiness of tumor blood vessels resulting in the flux of nanoparticles from the blood into the tumor tissue and reduced numbers of lymphatic vessels in tumors associated with decreased drainage of nanoparticles.

It has been determined that the histidine-lysine plasmid nanoplex transfected tumors efficiently (6). However, unlike most nanoparticles, it is likely that histidine-lysine nanoplexes do not depend on the enhanced permeability and retention mechanism but instead target neuropilin-1 (NRP-1). Because linear H2K peptides share a common amino acid sequence motif of —KXXK— (where X is any amino acid) with peptides that target neuropilin-1 and activate this pathway (6,7), the H2K nanoplex is likely transported through this pathway in the tumor. In addition, antibodies, which target neuropilin-1, almost completely block the uptake of the H2K nanoplexes into the tumor, further validating that these nanoplexes enter tumors through this pathway (6). By targeting neuropilin-1 with the H2K peptide, the nanoplexes intrinsically incorporate a tumor targeting ligand.

It has been determined that the histidine-lysine plasmid nanoplex transfected tumors efficiently. However, unlike most nanoparticles, it is likely that histidine-lysine nanoplexes do not depend on the enhanced permeability and retention mechanism but instead target neuropilin-1 (NRP-1). Because linear H2K peptides share a common amino acid sequence motif of —KXXK— (where X is any amino acid; SEQ ID NO: 1) with peptides that target neuropilin-1 and activate this pathway, the H2K nanoplex is likely transported through this pathway in the tumor. In addition, antibodies, which target neuropilin-1, almost completely block the uptake of the H2K nanoplexes into the tumor, further validating that these nanoplexes enter tumors through this pathway. By targeting neuropilin-1 with the H2K peptide, the nanoplexes intrinsically incorporate a tumor targeting ligand.

There is a recognized need in the art for improved formulations of doxorubicin. More specifically, there is a need for doxorubicin containing nanoplex formulations which deliver doxorubicin effectively to tumors and with greater antitumor activity. The present invention fulfills this longstanding need and desire in the art.

SUMMARY OF THE INVENTION

The present invention is directed to a tumor-targeting nanoplex. The tumor-targeting nanoplex comprises a chemotherapeutic agent DNA conjugate and a first tumor targeting-agent ionically linked to the chemotherapeutic agent DNA conjugate. The chemotherapeutic agent DNA conjugate comprises a chemotherapeutic agent intercalated with a plasmid DNA. The present invention is directed a related tumor-targeting nanoplex further comprising a second tumor-targeting agent conjugated to the tumor targeting nanoplex to enhance targeting.

The present invention also is directed to a method for treating a cancer in a subject. The method comprises administering to the subject a nanoplex comprising a chemotherapeutic agent DNA conjugate and a first tumor-targeting agent ionically linked to the chemotherapeutic agent DNA conjugate. The present invention is directed a related method where the nanoplex further comprises a second tumor-targeting agent as described herein.

The present invention is directed further to a tumor-targeting nanoplex. The tumor-targeting nanoplex comprises a doxorubicin plasmid DNA conjugate and a linear histidine-lysine peptide sequence ionically linked to the doxorubicin plasmid DNA conjugate. The doxorubicin plasmid DNA conjugate comprises doxorubicin intercalated to a p16shRaf1 plasmid. The present invention is directed a related tumor-targeting nanoplex further comprising a second tumor-targeting agent as described herein.

The present invention is further directed to a method for decreasing growth of a tumor in a cancer in a subject in need thereof. The method comprises administering to the subject a nanoplex comprising a doxorubicin plasmid DNA conjugate that comprises doxorubicin intercalated with a p16shRaf1 plasmid and a histidine-lysine peptide sequence as a first tumor-targeting agent. The histidine-lysine peptide is ionically ionically linked to the doxorubicin plasmid DNA conjugate. The present invention is directed to a related method where the nanoplex further comprises a second tumor-targeting agent as described herein.

Other and further aspects, features, and advantages of the present invention will be apparent from the following description of the presently preferred embodiments of the invention given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 2A shows the release profile of doxorubicin from nanoplex. At various times (1, 2, 4, 8 h), the nanoplexes were centrifuged with a filter (Microcon YM-50, Millipore, Billerica, MA) and fluorescence of the filtrate was then measured. At 8 h, release of doxorubicin from nanoplexes was minimal at pH 7.4 or pH 5.0. FIG. 2B shows release of doxorubicin from supercoiled or DNAse I-treated plasmids. Plasmids were incubated with DNAse I or control buffer (citrate buffer, 12.5 mM, pH-5) for 4 h. After DNAse treatment, half of the samples were treated with acidic isopropanol overnight at 40° C. to release doxorubicin from DNA. The remainder were treated with the citrate buffer. After overnight treatment, fluorescence was determined with a fluorimeter (Ex 489, Em 582 nm). N=2.

DETAILED DESCRIPTION OF THE PRESENT INVENTION

Figure 1:
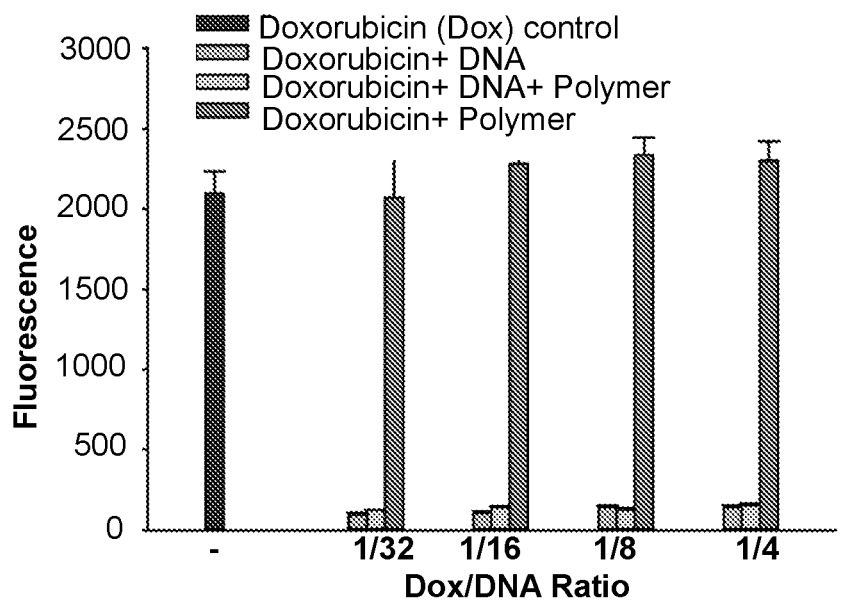
FIG. 1 shows that doxorubicin is intercalated in the nanoplex. Compared to doxorubicin alone, its fluorescence is significantly quenched with the addition of DNA. More than 95% of the fluorescence of doxorubicin was decreased at several ratios of doxorubicin:DNA (1:32, 1:16, 1:8, 1:4). With the addition of histidine-lysine peptides to the doxorubicin:DNA adduct, there was no effect on quenching. In the absence of DNA, the addition of the histidine-lysine peptide doxorubicin did not reduce fluorescence compared to doxorubicin alone.

For convenience, before further description of the present invention, certain terms employed in the specification, examples and appended claims are collected herein. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, components, method steps, and/or methods of the invention. It is contemplated that any composition, component or method described herein can be implemented with respect to any other composition, component or method described herein.

The term "or" in the claims refers to "and/or" unless explicitly indicated to refer to alternatives only or the alternatives are mutually exclusive, although the disclosure supports a definition that refers to only alternatives and "and/or".

The terms "comprise" and "comprising" are used in the inclusive, open sense, meaning that additional elements may be included.

The term "including" is used herein to mean "including, but not limited to". "Including" and "including but not limited to" are used interchangeably.

The term "about" is used herein to refer to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure. For example when referring to the size of the nanoplex, 45 nm to 275 nm is encompassed by about 50 nm to about 250 nm.

In one embodiment of the present invention, there is provided a first tumor targeting nanoplex comprising: a chemotherapeutic agent DNA conjugate comprising a chemotherapeutic agent intercalated to a plasmid DNA and a tumor targeting agent ionically linked to the chemotherapeutic agent DNA conjugate.

In addition to this embodiment, the tumor targeting nanoplex further comprises a second tumor-targeting agent conjugated to the tumor targeting nanoplex to enhance targeting thereof. In one preferred embodiment, the second tumor-targeting agent is a cRGD-PEG-H3K4b conjugate, RGD-PEG-H3K4b, NGR-PEG-H3K4b or CGKRK-PEG-H3K4b.

Preferably, the first tumor targeting agent is a linear histidine-lysine peptide sequence or a branched histidine-lysine peptide each comprising at least one —KHHK— sequence. A representative tumor-targeting agent may be a delivery agent. Representative chemotherapeutic agents include but are not limited to doxorubicin, epirubicin, daunorubicin or mitoxantrone.

Preferably, the chemotherapeutic agent and the plasmid DNA are in a wt/wt ratio of 1:2, 1:4, 1:8, 1:16, or 1:32. More preferred, the chemotherapeutic agent and plasmid DNA is in a ratio of 1:8 wt/wt. More preferably, the chemotherapeutic agent and the plasmid DNA are in a ratio of 1:16 wt/wt.

Also, in another preferred embodiment, the first tumor targeting agent and the plasmid DNA are in a wt/wt ratio of 1:2, 1:4, 1:6, or 1:8. More preferably, the first tumor targeting agent and the plasmid DNA are in a ratio of 1:2 wt/wt. In general, the nanoplex has a size of about 50 nm to about 250 nm.

In another embodiment of the present invention, there is provided a method of treating a cancer in a subject, comprising administering to the subject a nanoplex comprising a chemotherapeutic agent DNA conjugate comprising a chemotherapeutic agent intercalated with a plasmid DNA and a first tumor targeting agent ionically linked to the chemotherapeutic agent DNA conjugate.

In this embodiment, the nanoplex further comprises a second tumor-targeting agent conjugated to the tumor-targeting nanoplex to enhance targeting thereof. Preferably, the second tumor-targeting agent is cRGD-PEG-H3K4b, RGD-PEG-H3K4b, NGR-PEG-H3K4b, or CGKRK-PEG-H3K4b.

Preferably, the first tumor-targeting agent is a linear histidine-lysine peptide or a branched histidine-lysine peptide with at least one KHHK peptide sequence. The first tumor-targeting agent may be a delivery agent.

Representative examples of cancer which may be treated using this method include, but are not limited to, the cancer is a breast cancer, an ovarian cancer, a melanoma, a colon cancer, a pancreatic cancer, a brain cancer, a bladder cancer, a lung cancer, or a prostate cancer. In this embodiment, the representative chemotherapeutic agent is doxorubicin, epirubicin, daunorubicin or mitoxantrone. In this embodiment, the chemotherapeutic agent is administered in a therapeutically effective amount of about 0.016 mg/Kg to about 0.2 mg/Kg.

Further, in this embodiment the first tumor-targeting agent and the plasmid DNA are in a wt/wt ratio of 1:2, 1:4, 1:6, or 1:8. Preferably, the first tumor-targeting agent and the plasmid DNA are in a ratio of 1:2 wt/wt.

In one preferred embodiment, the chemotherapeutic agent and the plasmid DNA are in a wt/wt ratio of 1:2, 1:4, 1:8, 1:16, or 1:32. More preferably, the chemotherapeutic agent and plasmid DNA are in a ratio of 1:8 wt/wt. More preferably, the chemotherapeutic agent and plasmid DNA are in a ratio of 1:16 wt/wt. In general, the nanoplex has a size of about 50 nm to about 250 nm.

In yet another embodiment of the present invention, there is provided a tumor-targeting nanoplex comprising a doxorubicin plasmid DNA conjugate comprising doxorubicin intercalated to a p16shRaf1 plasmid; and a linear histidine-lysine peptide sequence ionically linked to the doxorubicin plasmid DNA conjugate.

In this embodiment, the tumor-targeting nanoplex further comprises a tumor-targeting agent conjugated to the tumor-targeting nanoplex to enhance targeting thereof. Preferably, the tumor-targeting agent is cRGD-PEG-H3K4b, RGD-PEG-H3K4b, NGR-PEG-H3K4b, or CGKRK-PEG-H3K4b. Preferably, the tumor-targeting agent is targetable to an $\alpha v\beta 3$ receptor, to an $\alpha v\beta 5$ receptor and to tumor vessels on the tumor. In general, the tumor-targeting agent binds through an ionic interaction to the histidine-lysine plasmid nanoplex and targets the $\alpha v\beta 3$ and $\alpha v\beta 5$ receptors on the tumor and tumor vessels.

Further, in this embodiment, the doxorubicin and the p16shRaf1 plasmid are in a wt/wt ratio of 1:8, 1:16, 1:32, or 1:64. Preferably, the doxorubicin and the p16shRaf1 plasmid are in a ratio of 1:16 wt/wt.

Preferably, the linear histidine-lysine peptide sequence and the p16shRaf1 plasmid are in a ratio of 1:2 wt/wt. In one preferred embodiment, the linear histidine-lysine peptide is targetable to a receptor on a tumor. Preferably, the receptor is a neuropilin-1 receptor. The nanoplex size range is about 50 nm to about 250 nm.

In yet another embodiment of the present invention, there is provided a method for decreasing growth of a tumor in a cancer in a subject in need thereof, comprising administering to the subject a nanoplex comprising a doxorubicin plasmid DNA conjugate comprising doxorubicin intercalated with a p16shRaf1 plasmid and a histidine-lysine peptide sequence as a first tumor-targeting agent ionically linked to the doxorubicin plasmid DNA conjugate.

In this embodiment, the nanoplex further comprises a second tumor-targeting agent ionically conjugated to the nanoplex to enhance targeting thereof. Preferably, the second tumor-targeting agent is cRGD-PEG-H3K4b, RGD-PEG-H3K4b, NGR-PEG-H3K4b, or CGKRK-PEG-H3K4b. Representative histidine-lysine peptides are a linear peptide or a branched peptide.

Representative tumors which are treated with this nanoplex include, but are not limited to, a breast cancer tumor, an ovarian cancer tumor, a melanoma, a pancreatic cancer tumor, a prostate cancer tumor, a brain cancer tumor, a colon cancer tumor, a bladder cancer tumor, or a lung cancer tumor. Preferably, the doxorubicin and the p16shRaf1 plasmid are in a wt/wt ratio of 1:8, 1:16, 1:32 or 1:64. More preferably, the doxorubicin and the p16shRaf1 plasmid are in a ratio of 1:16 wt/wt. In general, the nanoplex size is about 50 nm to about 250 nm. Preferably, the doxorubicin is in the nanoplex in an amount of about 0.016 mg/Kg to about 0.2 mg/Kg.

Provided herein are improved formulations of doxorubicin. The invention provided herein discloses a peptide-based doxorubicin containing nanoplex in which its uptake primarily depends on neuropilin-1 receptor targeting. The linear histidine lysine agent is both a delivery agent and a first targeting agent to target the neuropilin-1 receptor. The nanoplexes provided herein may comprise a second targeting agent. In a non-limiting example of a second targeting agent, cRGD-PEG-H3K4b is a cationic branched polymer that enhances delivery of the linear histidine lysine-plasmid DNA-chemotherapy nanoplex by targeting the avb3 and αvβ5 receptors or ligands. The cRGD-PEG-H3K4b binds to the negatively charged linear histidine lysine agent comprising the nanoplex through ionic interactions. Other such targeting agents are RGD-PEG-H3K4b, NGR-PEG-H3K4b, or CGKRK-PEG-H3K4b.

The nanoplexes provided herein increase the levels of doxorubicin in tumors by about 5.5-fold compared to aqueous (free) doxorubicin controls. Consistent with enhanced levels in the tumor, the nanoplex-doxorubicin treatment has significantly greater anti-tumor activity. Whereas low dose free doxorubicin does not reduce the size of tumors compared to untreated controls, the low dose nanoplex-doxorubicin reduces the size of tumors by nearly 55% ($p<0.001$). The high dose nanoplex-doxorubicin also inhibits the size of the tumor significantly more than the comparable high-dose free doxorubicin ($p<0.001$). Moreover, apoptosis and proliferation markers (Ki67) of tumors observed in the different treatment groups correlated with their ability to inhibit tumor size. The present invention demonstrates the efficacy of neuropilin-1 targeted nanoplexes to deliver doxorubicin to tumors in vivo.

A problem concerning liposome preparations, including DOXIL, is the inadequate release of doxorubicin in the tumor. Increased tumor levels of doxorubicin from the PEGylated liposomes in tumors do not always exhibit increased antitumor efficacy. For example, although PEGylated doxorubicin liposome preparation had a 3 to 4-fold greater accumulation than free doxorubicin in two different fibrosarcoma mouse models (8), free doxorubicin had greater antitumor activity in one of these models and only had marginally less activity in the other. It was suggested that the antitumor efficacy of DOXIL was partly limited by the reduced release of doxorubicin from the liposomes. To increase the bioavailability of doxorubicin from DOXIL, the copolymer P85 was administered at various times after mice with human ovarian cancer were given DOXIL (9). By disrupting the membranes of the liposomes, P85 aided in the release of doxorubicin from DOXIL. Although P85 administered 1 h after DOXIL significantly improved the antitumor efficacy, P85 given 48 hours after DOXIL was optimal. Unlike DOXIL, the antitumor activities of the free doxorubicin and the doxorubicin nanoplexes correlated closely with the levels of doxorubicin measured in the tumors. Despite these promising results, more PK studies are required for the histidine-lysine doxorubicin nanoplexes.

There are also potential disadvantages for nanoplexes that depend solely on enhanced permeability and retention for their entry into the tumor. Because blood vessel permeability may vary significantly within tumor tissue as well as between the primary and metastatic tumors, the antitumor efficacy of nanoplexes which depend solely on enhanced permeability and retention may be inconsistent (10). An alternative pathway of entry which enables the nanoplex to cross the vessel and traverse the tumor may circumvent this obstacle. A previous study provided strong evidence that the uptake of H2K polyplexes into the tumor was not dependent on enhanced permeability and retention but instead on the neuropilin-1 pathway (6). Whereas neuropilin-1 is frequently upregulated in tumor cells, neuropilin-1 expression is increased in nearly all tumor endothelial cells (11). Thus, even when the neuropilin-1 transport system of tumor cells is not increased, upregulation of neuropilin-1 in tumor endothelial cells ensures that the nanoplex traverses the vascular barrier of the tumor.

The current invention discloses that nearly 10% of the doxorubicin is within the tumor two hours after administering the high-dose doxorubicin nanoplex, which is significantly greater than levels from the free doxorubicin treatment. Levels of doxorubicin in the tumors correlated with the antitumor efficacy of the various treatment groups. The release of doxorubicin is accelerated as the plasmid DNA is degraded. Since nanoplexes protect plasmids from enzymatic degradation, these histidine lysine-plasmid-nanoplexes likely release doxorubicin with disassembly of the nanoplexes in the tumor. That doxorubicin is quickly released from the nanoplex is further validated by the statistically greater antitumor activity observed after the first injection of the doxorubicin-containing nanoplexes compared to free doxorubicin.

The current invention demonstrates an improvement in the tumor-targeted delivery of doxorubicin with a nanoplex. As shown herein, dose-dependency was observed in the therapeutic response. One could readily increase tumor levels of doxorubicin by increasing the amount of DNA delivered with each injection or by repeating the injections. The current approach used 8- to 16-fold lower amounts of a linear peptide compared to those of a branched peptide (12). Notably, even at higher dosages of branched peptide and their nanoplexes, no toxicity was observed in mice. Consequently, one would anticipate that increased amounts of nanoplexes comprised of the linear histidine lysine can be safely administered with greater antitumor efficacy.

Moreover, the use of plasmid-based therapy raises the possibility of gene therapy coupled with doxorubicin chemotherapy. The present invention demonstrated that doxorubicin incorporated into shRaf-1 expressing plasmids (doxorubicin:DNA-1/16 ratio) had a synergistic antitumor effect.

The current invention provides an effective yet easily assembled nanoplex formulation of doxorubicin with improved activity and without observed toxicity. Consistent with greater accumulation in tumors of doxorubicin, the nanoplex had a greater antitumor efficacy compared to free doxorubicin. Moreover, the enhanced tumor delivery of doxorubicin from the nanoplexes corresponds to greater apoptosis and reduced mitosis in treated tumor xenografts.

The following examples are given for the purpose of illustrating various embodiments of the invention and are not meant to limit the present invention in any fashion.

Example 1

Materials & Methods

Animals

Female athymic mice (4-8 weeks) were purchased from Envigo (Indianapolis, IN, USA). Animal experiments were performed in accordance with regulations by the Institutional Animal Care and Use Committee.

Cell Lines

The malignant cancer cell, MDA-MB-435, was cultured and maintained in DMEM with 10% fetal calf serum and 20 mM glutamine.

Plasmids

The pCpG-TdTomato (TdT) plasmid was prepared for systemic injection as described (13). The plasmids were purified with an EndoFree Maxi kit (Qiagen, Valencia, CA, USA). The p16shRaf1 plasmid was prepared by the elongation factor-1 (EF1) and H1 promoters in a CpG-free plasmid (InvivoGen) expressing the p16 gene product and the short hairpin Raf1 RNAi, respectively. Any general plasmid that has a promoter which expresses gene products, i.e., β-actin promoter, CMV, or short-hairpin RNAi, i.e., H1 or U6, in mammalian cells would be effective.

Peptides

The histidine lysine peptides may be linear or branched and comprise at least one KHHK motif (SEQ ID NO: 2). The linear histidine lysine peptides were synthesized by Genscript (Piscataway, NJ, USA). As detailed (5), sequences of histidine lysine peptides are the following: KHKHHKHHK—HHKHHKHHKHK-amide capped (H2K; SEQ ID NO: 3); KHKHHKHHKHHKHHKHHKHK—$CO_2H$ (H2K—$CO_2H$; SEQ ID NO: 4); KHHKHHKHHHKHHHKHHHKHHHKHHHKHHKHHK (H3K-33; SEQ ID NO: 5) (6). The cRGD-PEG-H3K4b conjugate was synthesized as described (6) with an average of 4 ligands per H3K4b molecule.

Doxorubicin Binding to DNA and Nanoparticle

Fluorescence of the doxorubicin solution (0.1 µg, 1.84 µM) was determined alone or after addition of plasmid DNA (3.2 µg, 1.6 µg, or 0.8 µg) for 30 minutes. Similarly, the fluorescence of doxorubicin in the nanoparticle was determined after addition of the histidine lysine peptide (H2K/H2KCO2H/H3K:wt/wt/wt:4.5/0.5/1) the doxorubicin:DNA conjugate for 40 min. To form the nanoparticle, the ratio of histidine lysine to plasmid DNA was about 1:2 (wt:wt). The fluorescence of doxorubicin was measured at an excitation of 489 and an emission of 582 nm (Synergy H1 microplate reader, Biotek, Winooski, VT, USA).

Release of Doxorubicin from the Nanoplex and Plasmids

The time-release profile of doxorubicin from the nanoplexes was determined by the recovered doxorubicin in the filtrate (14) using Microcon YM-50 filters (Millipore, Billerica, MA, USA). After measuring the fluorescence of doxorubicin in the filtrates, the percent of doxorubicin release was determined. In addition, release of doxorubicin from supercoiled and degraded plasmids (DNAseI, 4 units, 4 h) was determined. After incubation, control buffer or acidic isopropanol (which releases doxorubicin from DNA) was added overnight at 40° C. The fluorescence of these samples was then measured.

Histidine Lysine Nanoplexes Formation In Vivo

To the plasmid DNA (36 µg in 140 µl of water), histidine lysine (H2K/H2KCO2H/H3K: 11.25/1.25/2.5 µg in 110 µl water) was added quickly and mixed by pipetting. Forty-five minutes after mixing, cRGD-PEG-H3K4b (1.63 µg in 30 µl) was added to the nanoplex for 20 min prior to the intravenous injection of the nanoplex unless otherwise stated. Doxorubicin-containing histidine lysine nanoplexes were prepared similarly except that doxorubicin (2.2 or 4.4 µg) was added to the plasmid for 30 minutes at room temperature prior to the addition of the histidine lysine peptides.

Particle Size and Zeta Potential

The size (Z-A) and zeta potential of the nanoplexes were determined with the Zetasizer (Malvern, Westborough, MA, USA).

Doxorubicin Detection in Tumors In Vivo

When the tumors were approximately 150 mm3, the mice were injected intravenously with either free doxorubicin (4.4 µg) or doxorubicin-containing nanoplexes (2.2 or 4.4 µg of doxorubicin). Two hours after the injection of the different doxorubicin therapies, the mice were euthanized, and the amount of doxorubicin in tumors was determined (6 tumors per group). To quantitate doxorubicin in tumors, the acidic isopropanol method was used (15). The fluorescence of doxorubicin from the tumor extracts was measured at an excitation of 489 and an emission of 582 nm. A standard curve was created by adding known amounts of doxorubicin to tumor lysates (0.5, 0.25, 0.125 µg).

In Vivo Tumor Experiments

MDA-MB-435 cells (4×106 cells per injection) were subcutaneously injected bilaterally into each mouse. After 4 days, when the subcutaneous tumors were about 45 mm3, the mice were separated into groups of 6 mice to determine the efficacy of treatments. The groups were as follows: untreated, nanoplex alone, low dose doxorubicin (2.2 µg/injection), high dose doxorubicin (4.4 µg/injection, low dose doxorubicin nanoplex (2.2 µg/injection), high dose doxorubicin nanoplex (4.4 µg/injection). The mice were given five intravenous injections of the various treatments. Nanoplexes were administered every 2 to 3 days (Monday, Wednesday, Friday). Tumor size was assessed with calipers before each injection and 2 days after the last injection; the size was calculated by formula ½×d1×d22, where d2 is the smaller of the two measurements. Mice were weighed before each injection with tumor weight subtracted to obtain the final weight.

Histology of Tumor and Tissues

Two days after the last injection, mice were euthanized, and the deparaffinized tumors/tissues were stained with hematoxylin and eosin.

In Vivo Apoptosis of Tumors

The TUNEL assay was performed using the In Situ Cell Death Detection Kit (Roche Applied Science, Mannheim, Germany), following the manufacturer's instructions. After the tumors were incubated with TdT enzyme and label solution, the nuclei were stained with DAPI (Abcam, Cambridge, MA).

Immunofluorescence of Ki67

After the tumors were fixed and a heat-mediated antigen retrieval step was performed, the tumors were permeabilized (0.1% Triton X-100) for 10 min and then blocked with 5% BSA in 0.1% PBS-Tween for 2 h. The samples were then incubated with primary rabbit antibodies Ki67 (Abcam, ab 16667) or a monoclonal control (Abcam, ab 172730) at 1/200 dilution overnight at 4° C., followed by incubation at RT for 1 h with a goat anti-rabbit IgG (ALEXA FLUOR488) pre-adsorbed (ab150077) secondary antibody (shown in green). Nuclear DNA was labeled with DAPI.

Statistical Analysis

The results reported as mean±standard deviation represent at least 6 separate data measurements, unless otherwise indicated. Results were analyzed using a one-way ANOVA analysis with Holm-Sidak multiple pairwise comparisons posthoc test. P<0.05 was considered statistically significant.

Example 2

Doxorubicin is Incorporated within the Histidine Lysine Nanoplex

Upon doxorubicin binding to DNA, the fluorescence of doxorubicin is quenched enabling determination of entrapment efficiency (16). In FIG. 1, it was validated that the tdT plasmid could bind to doxorubicin as seen by quenching of its fluorescence. Upon binding to DNA, more than 95% of the fluorescence of doxorubicin is quenched at several doxorubicin:DNA ratios (1/32, 1/16, 1/8, and 1/4). Since doxorubicin is positively charged, it was investigated whether the addition of positively charged histidine lysine peptide would competitively compete with doxorubicin for the DNA. At low histidine lysine to DNA ratios (~1:2) to form nanoplexes, there was no evidence that doxorubicin was released from the DNA since quenching of the doxorubicin was maintained.

Size and Zeta Potential of the Nanoplexes

The particle size and zeta potential of different histidine lysine plasmid-doxorubicin nanoplexes were modestly different. The size of the histidine lysine nanoplex without doxorubicin was slightly smaller than those with doxorubicin. Although zeta potential of all the formulations had a negative surface charge, the zeta potential of the nanoplexes increased as more doxorubicin was added (Table 1). The size is dependent not only on the ratio of doxorubicin to DNA but also the ratio of the linear peptide:DNA, the concentration of the components and the salt concentration of the solution.

TABLE 1

Biophysical properties of histidine lysine polyplexes in vivo

| Doxorubicin/DNA[1] | Z-A[2] size (nm) | ζ Potential (mv) |
|---|---|---|
| —[3] | 145.8 ± 13.2 | −25.3 ± 6.4 |
| 1/16 | 157.1 ± 5.0 | −23.5 ± 3.2 |
| 1/8 | 172.8 ± 6.7 | −19.7 ± 4.7 |

Figure 2A:
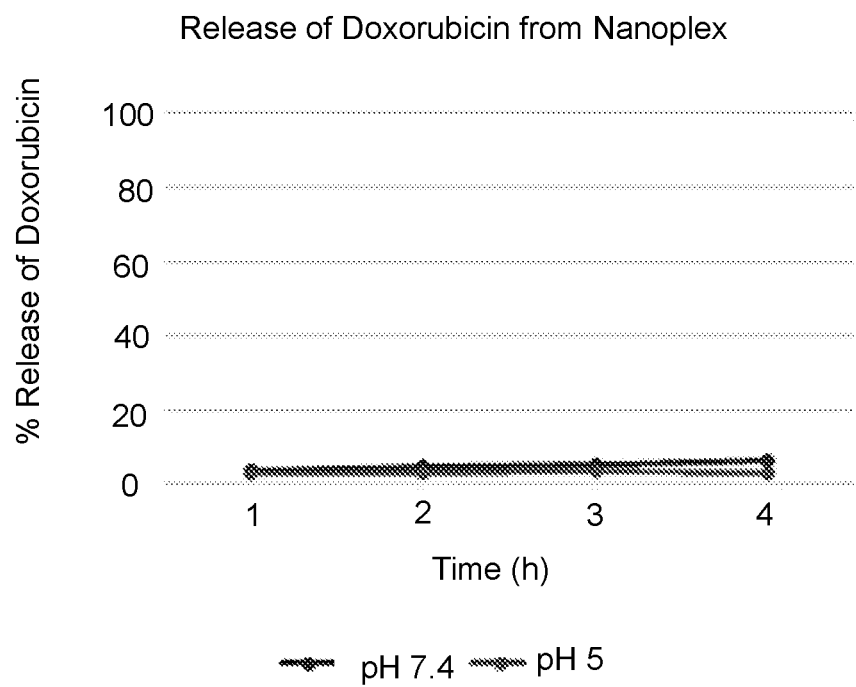
FIGS. 2A-2B shows the release profile of doxorubicin.
Figure 2B:
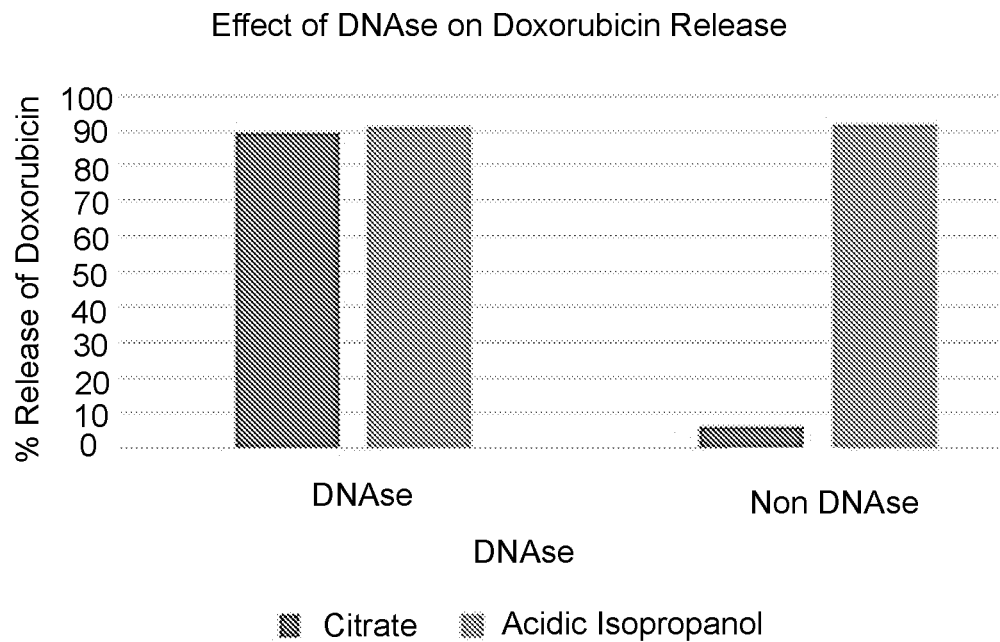

[1]Ratio of Doxorubicin: DNA (w/w)
[2]Z-A, size of the polyplex prepared in water
[3]No Doxorubicin added to the DNA plasmid sample Release of Doxorubicin The histidine lysine plasmid-doxorubicin nanoplex was stable up to 8 h to changes in the pH (pH 7.4 and 5.0). Less than 7% of doxorubicin was released under these conditions (FIG. 2A). However, degradation of the plasmid does markedly enhance the release of doxorubicin (FIG. 2B).

Figure 3:
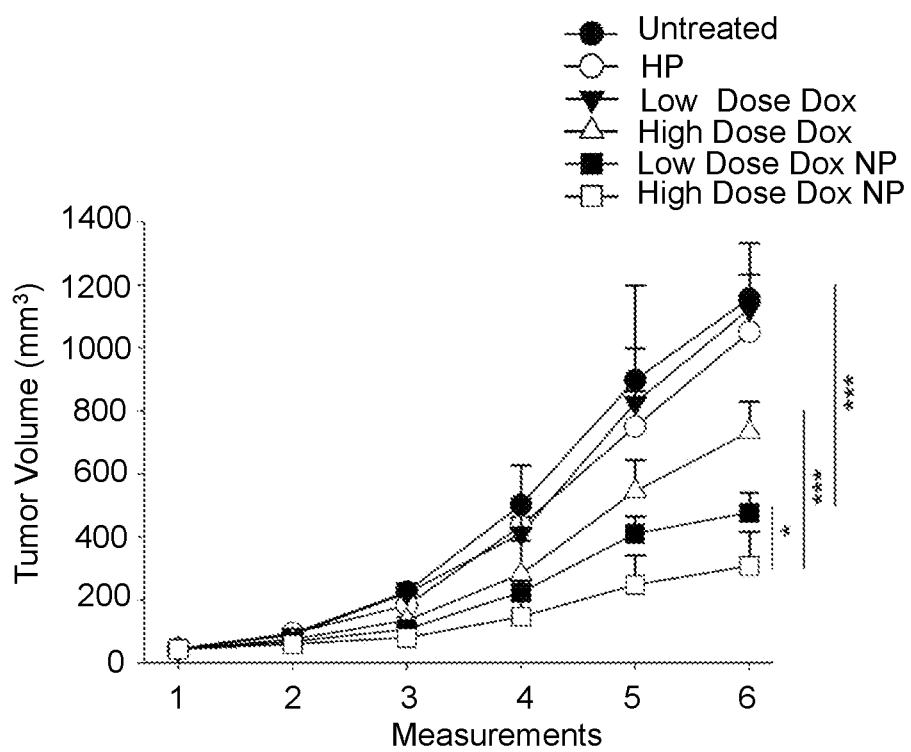
FIG. 3 shows that doxorubicin-containing nanoplexes significantly inhibited tumors. Four days after mice received injections of tumor cells, mice were divided into various treatment groups. Each group had six mice with 12 tumors, and tumors were measured prior to each injection. There were 5 injections with a final measurement 2 days after the last injection. At the sixth measurement, the low dose nanoplex (2.2 µg doxorubicin) and high dose nanoplex (4.4 µg doxorubicin) were significantly more effective than comparable dosages of free doxorubicin (p<0.001). The high dose nanaoplex inhibited tumor size by about 35% compared to the low dose nanoplex (p<0.05).

Doxorubicin-Containing Nanoplexes Inhibit the Size of Tumors Significantly More than Free Doxorubicin Because the linear histidine lysine nanoplexes previously showed poor uptake and activity in vitro yet marked antitumor activity in vivo (5), in vivo studies were done. The low dose nanoplex and high dose nanoplex had significantly more antitumor activity than comparable dosages of free doxorubicin (FIG. 3). Whereas the low dose doxorubicin had no effect on the growth of tumors, the low dose nanoplex inhibited the growth by about 60% at the sixth time point measurement (p<0.001). Similarly, the high dose nanoplex inhibited the size of tumors by about 58% compared to the high dose of free doxorubicin (p<0.001). Importantly, the doxorubicin-containing nanoplex showed a dose-dependency in their inhibition of the size of tumors. The high dose nanoplex inhibited the tumor size by about 35% more than the low dose nanoplex (p<0.01). The weekly human dose is about 0.016 mg/Kg to about 0.2 mg/Kg and the therapy may be administered once a week to two times a week intravenously.

Doxorubicin Levels in Tumors were Higher with the Nanoparticle

Figure 4:
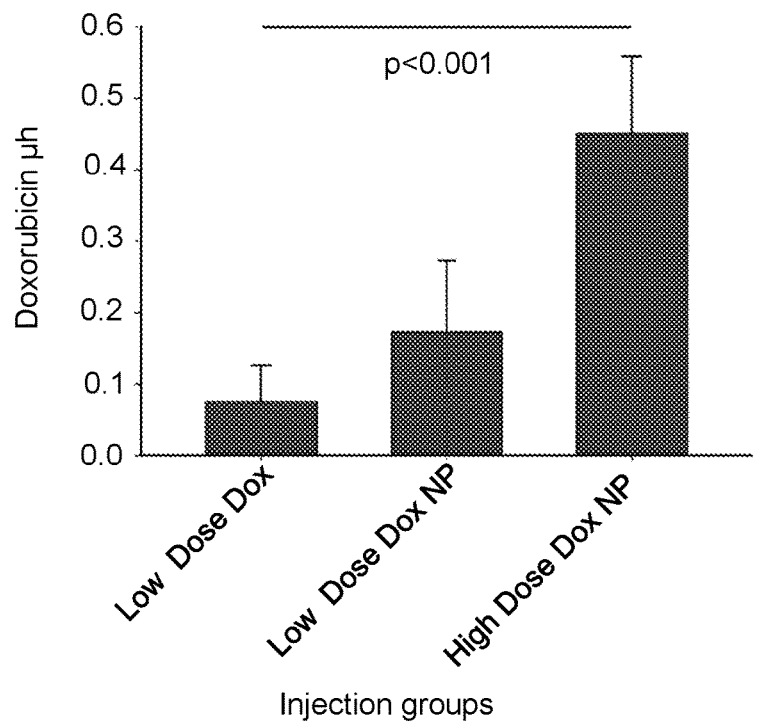
FIG. 4 shows tumor levels of doxorubicin were increased with nanoplex. When the tumors were approximately 150 mm3, the mice were injected intravenously with free doxorubicin (4.4 µg) or doxorubicin-containing nanoplexes (2.2 or 4.4 µg of doxorubicin). Two hours after injection of different doxorubicin therapies, the mice were euthanized, and the amount of doxorubicin in tumors (µg) was determined (6 tumors per group). The low and high dose nanoplex had increased levels of doxorubicin in the tumor compared to the free doxorubicin. Furthermore, the high dose doxorubicin nanoplex was significantly higher than the comparable free doxorubicin (p<0.001).

Consistent with the therapeutic response, the low dose and high-dose doxorubicin nanoplexes showed higher tumor levels of doxorubicin than comparable dosages of free doxorubicin (FIG. 4). The doxorubicin levels in tumors of the low dose and high dose nanoplex were approximately 2.4- and 5.5-fold higher than those of the high dose free-doxorubicin. The doxorubicin levels of the high-dose histidine lysine nanoplex were statistically different than those of the free doxorubicin (p<0.001).

Figure 5:
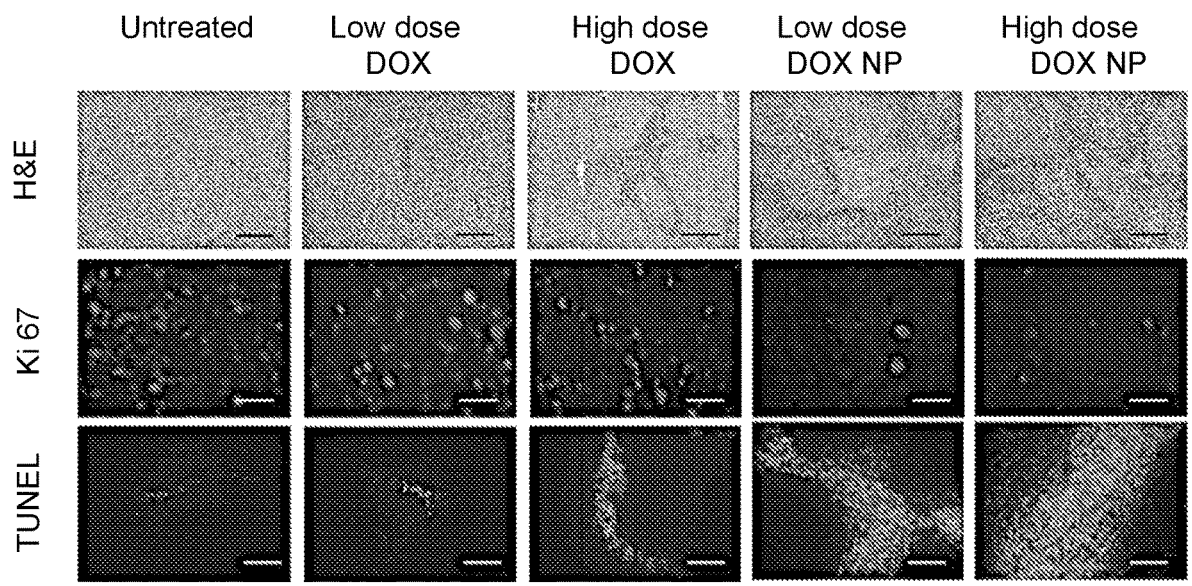
FIG. 5 shows in vivo histology of tumors with H&E staining, Ki67 and TUNEL. After the last treatment injection, mice were euthanized, and tumor sections were stained with hematoxylin and eosin. There was significantly greater tumor necrosis in mice treated with doxorubicin-containing nanoplexes. Scale bars, 20 µM (Upper panels). Immunofluorescent detection of Ki67. A fluorescent secondary antibody was used to visualize the primary antibody binding. There were increases in Ki67 expression in the free doxorubicin treatment groups compared to doxorubicin-containing nanoplex. Scale bars, 10 µM (Middle panels). Apoptosis of tumor-induced by various treatment groups with the TUNEL assay. Increased apoptosis was observed in doxorubicin-containing nanoplexes. Scale bars, 20 µM (lower panels).
Figure 6:
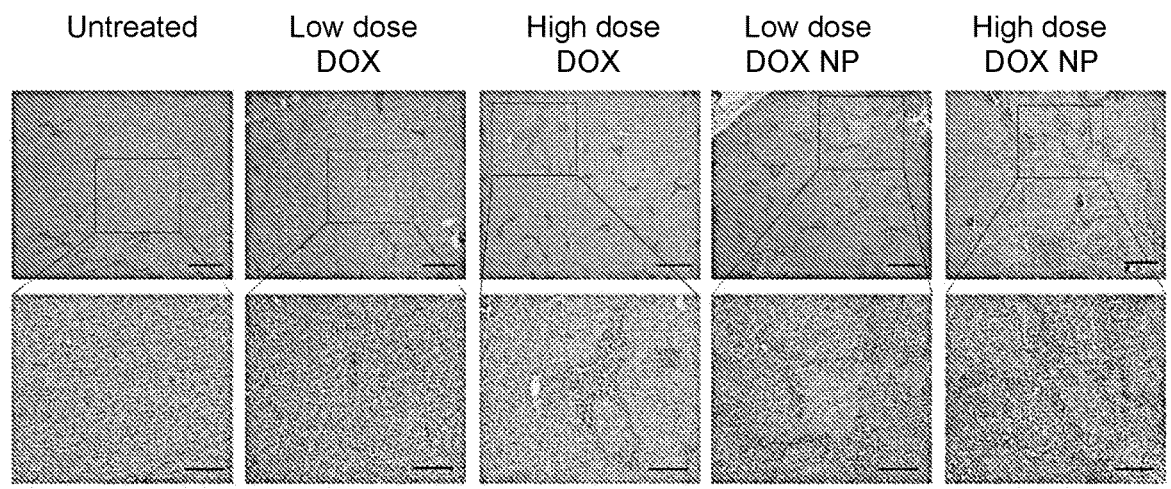
FIG. 6 shows histology of tumors with H&E staining. Upper and bottom (inserts) panels represent histology of tumors treated with various therapies. Bottom panels show higher-magnification views of the necrotic tissue area. Scale bars (top)=50 µm, (bottom)=20 µm.
Figure 7:
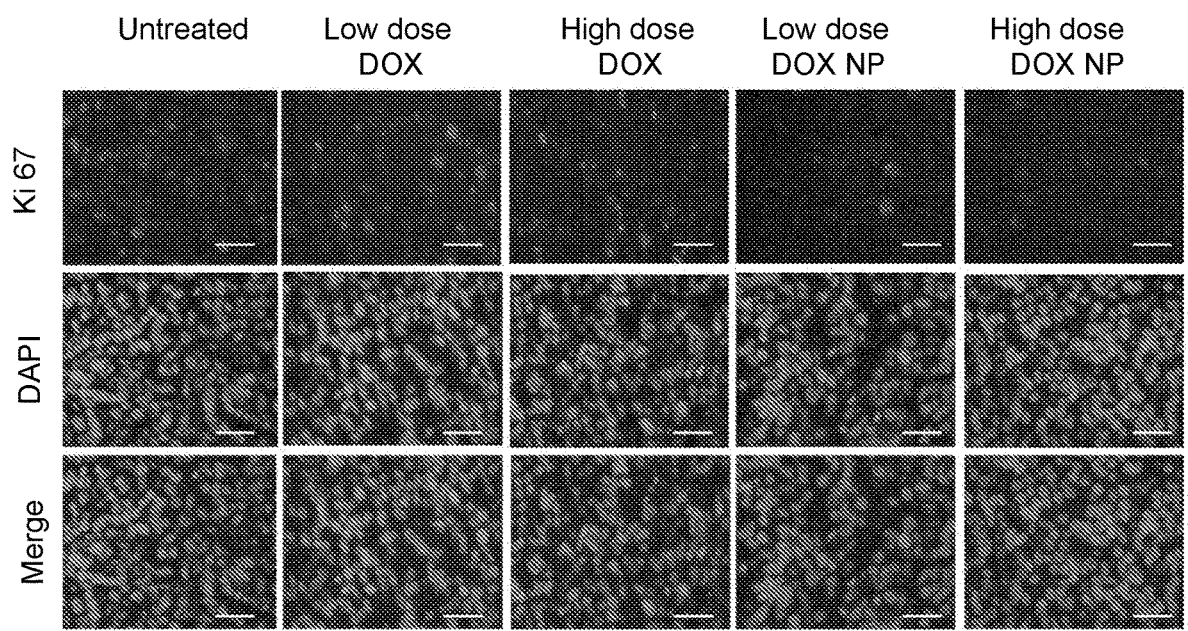
FIG. 7 shows detection of Ki67 in the tumor. Immunofluorescence of Ki67 (upper panel), nuclear DNA was labeled with DAPI (middle panel) and lower panel (merge image of Ki67 and DAPI staining). Scale bars=10 µm.
Figure 8:
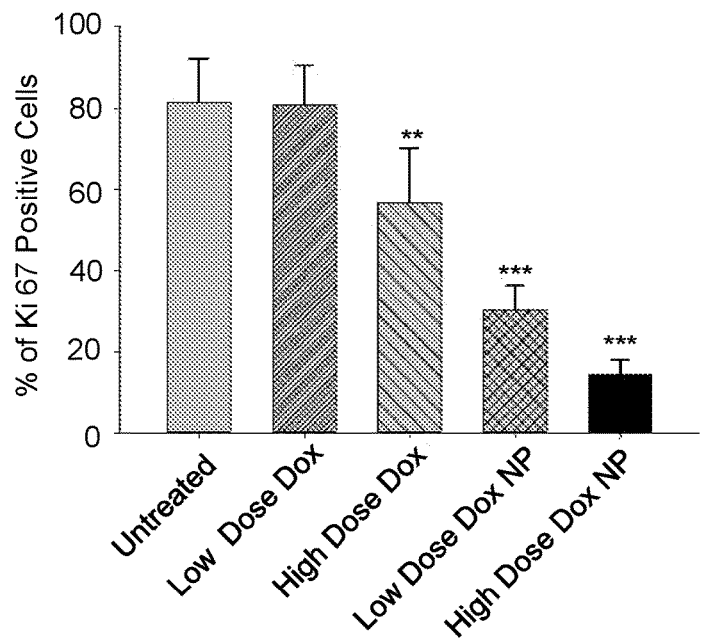
FIG. 8 shows percentage of Ki67 positive cells. Quantification of tumor cells staining positive for Ki67 with different treatment groups is shown, expressed as the percentage of Ki67 positive cells. The data represent the mean+SD of four HPF images (60×) for each treatment. , $p<0.01$, *, $p<0.001$. N=~50 cells/image.
Figure 9:
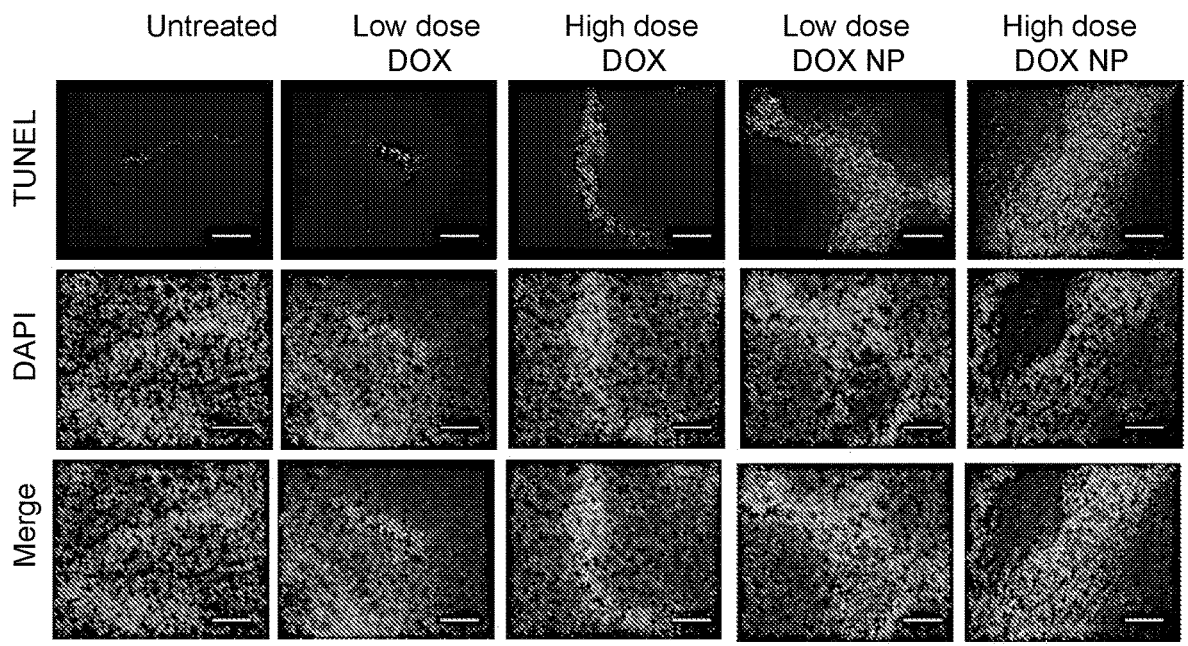
FIG. 9 shows tumor apoptosis. The apoptosis in mice tumor tissues was evaluated by fluorescence TUNEL staining (upper panel), nuclear DNA was labeled with DAPI (middle panel), merge image of TUNEL and DAPI staining (lower panel). Scale bars=20 µm.

Reduced Growth and Enhanced Apoptosis in Tumors Treated with Doxorubicin-Containing Nanoplexes The histology, apoptosis, and mitotic index of tumors closely correlated to therapeutic responses with the different therapies. H&E staining showed large areas of necrosis in doxorubicin-nanoplexes compared to the comparable free doxorubicin (FIGS. 5-6). The expression of Ki67, a marker of proliferation, and apoptosis were also analyzed in tumor sections (FIG. 5 and FIG. 7-9). It was found that about 30% of the tumor cells in the low dose doxorubicin nanoplex stained positive for Ki67 compared to 80% of cells in the low dose free doxorubicin group. Moreover, only 14% of the tumor cells in the high dose doxorubicin nanoplex group stained positive for Ki67 whereas about 57% of cells stained positive in the high dose free doxorubicin group (FIG. 4 and FIG. 8). In addition, enhanced apoptosis, as demonstrated by the positive TUNEL staining, was observed in the tumors of mice treated with the doxorubicin containing nanoplexes (FIG. 4 and FIG. 9). Thus, both decreased proliferation and increased apoptosis accounted for the reduction in tumor size with the doxorubicin-containing nanoplexes compared to free doxorubicin group.

Toxicity

Figure 10:
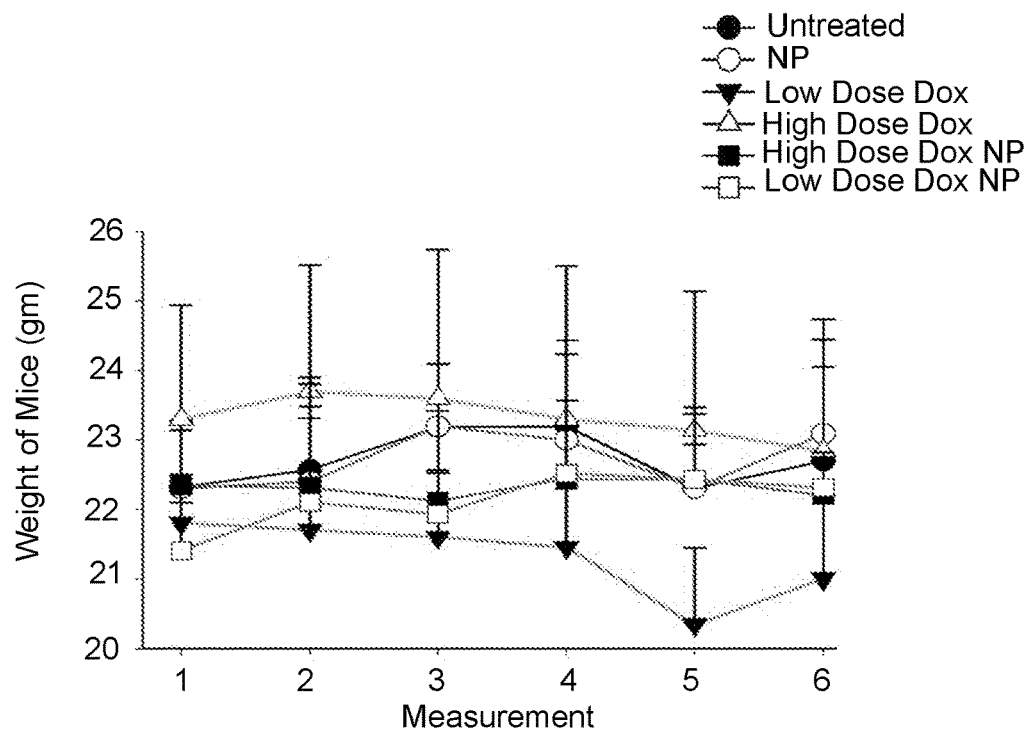
FIG. 10 shows weight of mice during treatment. The weight of mice was measured prior to each injection and 2 days prior after last injection.

At the dosages used, no weight loss or other adverse effects were observed with doxorubicin-nanoplexes (FIG. 10). Furthermore, no histological evidence of toxicity was found in normal tissues (heart, liver, lungs, spleen, and kidneys) from animals treated with either low or high dose doxorubicin-nanoplexes.

Example 3

MDA-MD-MB Tumors are Inhibited by p16shRAF-1 Doxorubicin Nanoplex

Figure 11:
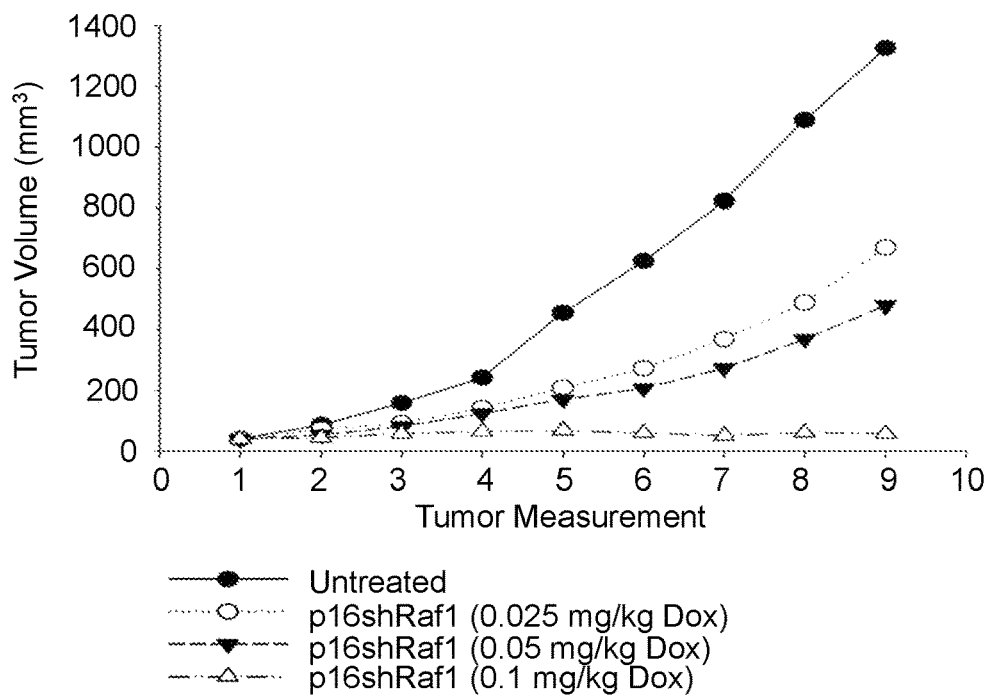
FIG. 11 shows that MDA-MB-435 xenografts were inhibited by p16shRaf1 and doxorubicin.

Various ratios of doxorubicin to the p16shRaf1 plasmid were examined for their antitumor efficacy. At the highest ratio of doxorubicin to plasmid DNA (1:16; dose of doxorubicin per injection-0.1 mg/kg), there was complete inhibition of the tumor. At lower doxorubicin to plasmid DNA ratios (1:32, 1:64), there was less inhibition of the tumor size. Although treatment groups varied in the doxorubicin: DNA ratios, the nanoplexes were all comprised of histidine-lysine peptides (~15 mg) and plasmids (~35 mg). The MDA-MD-MB tumors were established subcutaneously and were approximately 40 mm³ in size when treatment was begun. The nanoplexes, in which doxorubicin was incorporated, were administered intravenously every 2 to 3 days. With the exception of nanoplex containing the highest dose of doxorubicin (0.1 mg/kg doxorubicin), the tumor-bearing mice received an intravenous (iv) injection before each measurement. The tumor-bearing mice receiving the highest dose of doxorubicin (0.1 mg/kg doxorubicin) received nanoplexes iv except for the 6th and 7th measurement (indicated by the X) (FIG. 11).

The following references are cited herein.
1. Carvalho et al. Curr Med Chem 2009; 16:3267-85.
2. Singal et al. New England Journal of Medicine 1998; 339:900-05.
3. Rafiyath et al. Exp Hematol Oncol 2012; 1:10.
4. Laginha et al. Clin Cancer Res 2005; 11: 6944-9.
5. Ngan et al. Archives of Pharmacy Practice 2016; 7:1-13.
6. Leng et al. J Gene Med 2016; 18:134-44.
7. Teesalu et al. Proc Natl Acad Sci USA 2009; 106:16157-62.
8. Mayer et al. J Pharmacol Exp Ther 1997; 280:1406-14.
9. Zhao et al. J. Control Release 2013; 168:61-9.
10. Karathanasis et al. PLoS One 2009; 4:e5843.
11. Akashi et al. Br J Cancer 2014; 110:1481-7.
12. Leng et al. J Gene Med 2006; 8:1407-15.
13. Leng et al. J Gene Med 2014; 16:317-28.
14. Xia et al. Biochemistry 2016; 55:1326-31.
15. Laginha et al. Clin Cancer Res 2005; 11:6944-9.
16. Charbgoo et al. Nanomedicine 2018; 14: 685-97.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. The terms in the claims have their plain, ordinary meaning unless otherwise explicitly and clearly defined by the patentee.

What is claimed is:

1. A tumor-targeting nanoplex, comprising:
a chemotherapeutic agent DNA conjugate comprising a chemotherapeutic agent intercalated to a plasmid DNA; and
a first tumor-targeting agent that is a linear histidine-lysine peptide sequence comprising at least one —KHHK— (SEQ ID NO: 2) peptide ionically linked to the chemotherapeutic agent DNA conjugate.

2. The tumor-targeting nanoplex of claim 1, further comprising a second tumor-targeting agent conjugated to the tumor targeting nanoplex to enhance targeting thereof.

3. The tumor-targeting nanoplex of claim 2, wherein the second tumor-targeting agent is cRGD-PEG-H3K4b, RGD-PEG-H3K4b, NGR-PEG-H3K4b, or CGKRK-PEG-H3K4b.

4. The tumor-targeting nanoplex of claim 1, wherein the tumor-targeting agent is a delivery agent.

5. The tumor-targeting nanoplex of claim 1, wherein the chemotherapeutic agent is doxorubicin, epirubicin, daunorubicin, or mitoxantrone.

6. The tumor-targeting nanoplex of claim 1, wherein the chemotherapeutic agent and the plasmid DNA are in a wt/wt ratio of 1:2, 1:4, 1:8, 1:16, or 1:32.

7. The tumor-targeting nanoplex of claim 6, wherein the chemotherapeutic agent and the plasmid DNA are in a ratio of 1:8 wt/wt.

8. The tumor-targeting nanoplex of claim 6, wherein the chemotherapeutic agent and the plasmid DNA are in a ratio of 1:16 wt/wt.

9. The tumor-targeting nanoplex of claim 1, wherein the first tumor targeting agent and the plasmid DNA are in a wt/wt ratio of 1:2, 1:4, 1:6, or 1:8.

10. The tumor-targeting nanoplex of claim 9, wherein the first tumor targeting agent and the plasmid DNA are in a ratio of 1:2 wt/wt.

11. The tumor-targeting nanoplex of claim 1, wherein the nanoplex has a size of about 50 nm to about 250 nm.

12. A method for treating a cancer in a subject, comprising administering to the subject a nanoplex comprising a chemotherapeutic agent DNA conjugate comprising a chemotherapeutic agent intercalated with a plasmid DNA and a first tumor-targeting agent that is a linear histidine-lysine peptide sequence comprising at least one —KHHK— (SEQ ID NO: 2) peptide ionically linked to the chemotherapeutic agent DNA conjugate.

13. The method of claim 12, wherein the nanoplex further comprises a second tumor-targeting agent conjugated to the tumor-targeting nanoplex to enhance targeting thereof.

14. The method of claim 13, wherein the second tumor-targeting agent is cRGD-PEG-H3K4b, RGD-PEG-H3K4b, NGR-PEG-H3K4b, or CGKRK-PEG-H3K4b.

15. The method of claim 12, wherein the first tumor-targeting agent is a delivery agent.

16. The method of claim 12, wherein the cancer is a breast cancer, an ovarian cancer, a melanoma, a colon cancer, a pancreatic cancer, a brain cancer, a bladder cancer, a lung cancer, or a prostate cancer.

17. The method of claim 12, wherein the chemotherapeutic agent is doxorubicin, epirubicin, daunorubicin or mitoxantrone.

18. The method of claim 12, wherein the chemotherapeutic agent is administered in a therapeutically effective amount of about 0.016 mg/Kg to about 0.2 mg/Kg.

19. The method of claim 12, wherein the first tumor-targeting agent and the plasmid DNA are in a wt/wt ratio of 1:2, 1:4, 1:6, or 1:8.

20. The method of claim 19, wherein the first tumor-targeting agent and the plasmid DNA are in a ratio of 1:2 wt/wt.

21. The method of claim 12, wherein the chemotherapeutic agent and the plasmid DNA are in a wt/wt ratio of 1:2, 1:4, 1:8, 1:16, or 1:32.

22. The method of claim 21, wherein the chemotherapeutic agent and plasmid DNA are in a ratio of 1:8 wt/wt.

23. The method of claim 21, wherein the chemotherapeutic agent and the plasmid DNA are in a ratio of 1:16 wt/wt.

24. The method of claim 12, wherein the nanoplex has a size of about 50 nm to about 250 nm.

* * * * *